(12) United States Patent
Bhakoo et al.

(10) Patent No.: US 6,471,947 B2
(45) Date of Patent: Oct. 29, 2002

(54) ORAL COMPOSITION

(75) Inventors: Manmohan Bhakoo, Bebington (GB); Andrew Joiner, Bebington (GB); Karen Anne Steele, Bebington (GB); David Taylor, Bebington (GB); Katherine Mary Thompson, Bebington (GB); David William Thornthwaite, Bebington (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/050,970

(22) Filed: Jan. 16, 2002

(65) Prior Publication Data

US 2002/0136698 A1 Sep. 26, 2002

(30) Foreign Application Priority Data

Jan. 16, 2001 (EP) .............................. 01300336

(51) Int. Cl.$^7$ .............................. A61K 7/16; A61K 7/18; A61K 7/20
(52) U.S. Cl. .............................. 424/53; 424/49; 424/52
(58) Field of Search .............................. 424/53

(56) References Cited

U.S. PATENT DOCUMENTS

| | | | | |
|---|---|---|---|---|
| 2,624,655 A | * | 1/1953 | Greenspan ................. 23/207.5 |
| 3,156,654 A | * | 11/1964 | Konecny et al. .............. 252/95 |
| 3,671,439 A | * | 6/1972 | Corey et al. .................. 252/99 |
| 4,105,759 A | * | 8/1978 | Schreiber et al. ............. 424/52 |
| 4,992,194 A | * | 2/1991 | Liberati et al. ............... 252/99 |
| 5,073,285 A | * | 12/1991 | Liberati et al. ............... 252/94 |
| 5,098,598 A | * | 3/1992 | Sankey et al. ......... 252/186.42 |
| 5,266,587 A | * | 11/1993 | Sankey et al. .............. 514/417 |
| 5,435,808 A | | 7/1995 | Holzhauer et al. ............ 8/94.18 |
| 5,463,112 A | * | 10/1995 | Sankey et al. ................. 562/2 |
| 5,466,825 A | * | 11/1995 | Carr et al. .................. 348/479 |
| 5,914,303 A | * | 6/1999 | Sankey et al. .............. 510/310 |
| 5,985,815 A | * | 11/1999 | Townend et al. ........... 510/313 |
| 5,997,764 A | * | 12/1999 | Ambuter et al. ........ 252/186.25 |
| 6,083,422 A | * | 7/2000 | Ambuter et al. ........ 252/187.26 |
| 6,096,098 A | * | 8/2000 | Miracle et al. ................ 88/111 |
| 6,117,357 A | * | 9/2000 | Kott et al. ............. 252/186.38 |
| 6,165,448 A | * | 12/2000 | Joiner et al. .................. 424/49 |
| 6,218,352 B1 | * | 4/2001 | Lee et al. .................... 510/375 |
| 6,291,413 B1 | * | 9/2001 | Miracle et al. ............. 510/313 |
| 6,350,437 B1 | * | 2/2002 | Pasetti et al. .................. 424/53 |

FOREIGN PATENT DOCUMENTS

| | | |
|---|---|---|
| CA | 984 755 | 3/1976 |
| DE | 39 42 643 | 12/1989 |
| EP | 0 325 288 | 7/1989 |
| EP | 0 325 289 | 7/1989 |
| EP | 0 485 927 | 11/1990 |
| EP | 545 594 | 6/1993 |
| EP | 0 666 307 | 8/1995 |
| EP | 0 845 526 | 6/1998 |
| EP | 906 950 | 4/1999 |
| EP | 1 010 750 | 6/2000 |
| EP | 0 074 607 | 2/2001 |
| WO | 90/07501 | 7/1990 |
| WO | 96/05802 | 2/1996 |

OTHER PUBLICATIONS

PCT International Search Report in a PCT application PCT/EP 01/14496 May 2002.

* cited by examiner

Primary Examiner—Shep K. Rose
(74) Attorney, Agent, or Firm—Milton L. Honig

(57) ABSTRACT

An oral composition comprising picolinic acid and a peroxyl species or equivalent source thereof, characterised in that the molar ratio of picolinic acid to peroxyl species or equivalent source thereof is from 1:30 to 100:1.

12 Claims, No Drawings

ORAL COMPOSITION

BACKGROUND OF THE INVENTION

1. Field of the Invention

The present invention relates to an oral composition containing peroxides.

2. The Related Art

Peroxyl species, in particular hydrogen peroxide and sources thereof, are well-known antimicrobial agents, although they have not been widely used in deodorant products for use on the human body. It is also known that the stability of such materials can be improved by the addition of small amounts of transition metal chelator. The use of dipicolinic acid for such purpose is described in several publications, for example EP 666,307 A (Procter and Gamble). Dipicolinic acid is also claimed to improve the antimicrobial effect hydrogen peroxide—see EP 845,526 A (Eka Chemicals).

Picolinic acid has been described in WO9007501 (Solvay Interox) as a stabiliser for percarboxylic acid bleaching compositions. The picolinic acid is added in minor amounts to sequester transition metals which catalyse peroxygen compound decomposition. Picolinic acid is also listed as an optional component for this purpose in EP 1,074,607 (Ausimont S.p.A.).

SUMMARY OF THE INVENTION

We have discovered that synergistic mixtures of picolinic acid and a peroxyl species or equivalent source thereof can achieve the target of providing an excellent antimicrobial benefit and subsequent protection against plaque, caries and gingivitis. We have also found that synergistic mixtures of picolinic acid and a peroxyl species or equivalent source thereof can achieve the target of providing an excellent tooth whitening benefit.

None of the prior art discloses or suggests the products of the present invention, nor the excellent antimicrobial and tooth whitening benefits obtainable by the use thereof.

DETAILED DESCRIPTION OF THE INVENTION

We have found that use of a synergistic mixture of picolinic acid and a peroxyl species or equivalent source thereof gives an excellent tooth whitening antimicrobial benefit—much greater than that obtained from either of the two components individually. In addition, the addition of picolinic acid at such a level as to give said synergistic benefit enables less of the peroxyl species or equivalent source thereof to be used in the product—a significant benefit for products used on the human body.

Thus, in a first aspect of the invention, there is provided an oral composition comprising picolinic acid and a peroxyl specifes or equivalent source thereof, wherein the molar ratio of picolinic acid to peroxyl species or equivalent source thereof is from 1:30 to 100:1.

In a second aspect of the present invention, there is provided a cosmetic method of whitening the teeth comprising the use of picolinic acid and a peroxyl species or equivalent source thereof.

In a third aspect of the present invention, there is provided a method for the manufacture of an oral composition for the treatment of gingivitis, caries and/or plaque by mixing picolinic acid and a peroxyl species or equivalent source thereof with a cosmetically acceptable carrier material.

The antimicrobial and tooth whitening benefit derived from use of the present invention may be gained by independent application of picolinic acid and the peroxyl species or equivalent source thereof. Such application may be concurrent or consecutive, provided that the treated substrate experiences the presence of both components at the same time. When the components are applied from independent compositions, it is preferred that the product also comprises a means for, and/or instruction for, both of the compositions to be applied to the human body. Where the peracid and picolinic acid are stored independently from one another the formulatory requirements may be such that the stability of either is optimised. For example, if one formulation comprises a peracid such as PAP the pH of the formulation will be between 3.5 and 5, preferably 4. The formulation of the formulation comprising picolinic acid will then be modified such that when the two components are mixed they provide an oral composition according to the invention and having an acceptable pH of between 6.5 and 7.5.

It is preferred that the picolinic acid and the peroxyl species or equivalent source thereof are applied from the same composition. A preferred product according to the invention is a single composition comprising both the picolinic acid and the peroxyl species or equivalent source thereof.

The cosmetic method of gaining an antimicrobial benefit on the human body referred to in the second aspect of the present invention preferably uses the picolinic acid and the peroxyl species or equivalent source thereof at a molar ratio of from 1:30 to 100:1. This molar ratio, and that present in the composition according to the first aspect of the invention, is more preferably from 1:20 to 50:1 and most preferably from 1:10 to 20:1.

Picolinic acid is an essential component in the products of the invention. It may be used at a level of from 0.01% to 10%, particularly from 0.1% to 8%, and especially from 0.15% to 5%, by weight based on total weight of the composition. The picolinic acid may be used in its acid form or as its salt. Suitable salts include alkaline metal salts, alkaline earth metal salts, amine salts, and quaternary ammonium salts. When the picolinic acid is partially or totally in its salt form, the preferred amount is equivalent to the aforementioned preferred levels, on a molar basis.

The products of the invention comprise a peroxyl species per se or a material that generates a peroxyl species in situ. A peroxyl species is one that comprises a peroxy (—O—O—) group. Examples of suitable peroxyl species include hydrogen peroxide and peracids. Examples of equivalent sources thereof are compounds that produce hydrogen peroxide on dissolution in water, such as sodium perborate monohydrate, sodium perborate tetrahydrate, sodium percarbonate and percarbamide (urea-hydrogen peroxide addition compound). Further examples are enzymatic hydrogen peroxide generating systems such as peroxidases, oxidases and other oxido-reductase enzyme systems, in conjunction with their appropriate substrates. Preferred products comprise a peracid, in particular a peracid of formula (1)

(1)

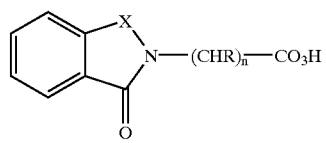

in which R is hydrogen or $C_1$–$C_4$ alkyl; n is 1 to 5; and X is C=O or $SO_2$.

The peroxy amido phthalamides of formula 1) are known per se and have been described in EP-A-325,288 and EP-A-325,289. A preferred compound of this formula is N-phthalimido hexanoic peroxy acid ("PAP") of formula 1), in which R=H, n=5 and x=C=0. An example of a compound according to formula 1) wherein $x=SO_2$ is saccharin-perhexanoic acid ("saccharin PAP"), as described in EP-A-485,927. Alternatively, a compound that produces hydrogen peroxide on dissolution in water, rather than hydrogen peroxide itself. Suitable peracids include any of those mentioned in WO96/05802 the contents relating to peracids being hereby incorporated by reference.

Particularly preferred products comprise a compound that produces hydrogen peroxide on dissolution in water, especially products from which hydrogen peroxide is absent, prior to application.

The amount of peroxyl species or equivalent source thereof in compositions of the invention may range from 0.0001% to 5%, more preferably from 0.001 to 1.5%, most preferably from 0.005% to 0.5%, by weight based on total weight of the composition.

Where the oral composition is to be used for its antimicrobial effect the composition may also comprise a transition metal chelator. Whilst picolinic acid is a transition metal chelator, performance may be increased by the use of a further material of this class, in particular a material having a high binding constant for iron (III); that is to say, a binding constant for iron (III) of greater than $10^{15}$, preferably greater than $10^{20}$, and most preferably greater than $10^{26}$. A particularly preferred material of this class is diethylenetriamine-pentaacetic acid (DTPA). Salts of such materials may also be employed, suitable salts being analogous to those described as suitable picolinic acid salts (vide supra). The total amount of additional transition metal chelator and salt thereof that is employed is typically from 0.1% to 5%, in particular from 0.2% to 3%, and especially from 0.4% to 2% by weight of the composition of which it is a part.

The oral composition according to the invention comprise further ingredients which are common in the art, such as:

- antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2'methylenebis-(4-chloro-6-bromophenol);
- anti-inflammatory agents such as ibuprofen, flurbiprofen, aspirin, indomethacin etc.;
- anti-caries agents such as sodium- and stannous fluoride, aminefluorides, sodium monofluorophosphate, sodium trimeta phosphate and casein;
- plaque buffers such as urea, calcium lactate, calcium glycerophosphate and strontium polyacrylates;
- vitamins such as Vitamins A, C and E;
- plant extracts;
- desensitising agents, e.g. potassium citrate, potassium chloride, potassium tartrate, potassium bicarbonate, potassium oxalate, potassium nitrate and strontium salts;
- anti-calculus agents, e.g. alkali-metal pyrophosphates, hypophosphite-containing polymers, organic phosphonates and phosphocitrates etc.;
- biomolecules, e.g. bacteriocins, antibodies, enzymes, etc.;
- flavours, e.g. peppermint and spearmint oils;
- proteinaceous materials such as collagen;
- preservatives;
- opacifying agents;
- colouring agents;
- pH-adjusting agents;
- sweetening agents;
- pharmaceutically acceptable carriers, e.g. starch, sucrose, water or water/alcohol systems etc.;
- surfactants, such as anionic, nonionic, cationic and zwitterionic or amphoteric surfactants;
- particulate abrasive materials such as silicas, aluminas, calcium carbonates, dicalciumphosphates, calcium pyrophosphates, hydroxyapatites, trimetaphosphates, insoluble hexametaphosphates and so on, including agglomerated particulate abrasive materials, usually in amounts between 3 and 60% by weight of the oral care composition.
- humectants such as glycerol, sorbitol, propyleneglycol, xylitol, lactitol etc.;
- binders and thickeners such as sodium carboxymethylcellulose, xanthan gum, gum arabic etc. as well as synthetic polymers such as polyacrylates and carboxyvinyl polymers such as Carbopol®;
- polymeric compounds which can enhance the delivery of active ingredients such as antimicrobial agents can also be included. Examples of such polymers are copolymers of polyvinylmethylether with maleic anhydride and other similar delivery enhancing polymers, e.g. those described in DE-A-3,942,643 (Colgate);
- buffers and salts to buffer the pH and ionic strength of the oral care composition; and
- other optional ingredients that may be included are e.g. bleaching agents such as peroxy compounds e.g. potassium peroxydiphosphate, effervescing systems such as sodium bicarbonate/citric acid systems, colour change systems, and so on.

Liposomes may also be used to improve delivery or stability of active ingredients.

The oral compositions may be in any form common in the art, e.g. toothpaste, gel, mousse, aerosol, gum, lozenge, powder, cream, etc. and may also be formulated into systems for use in dual-compartment type dispensers.

EXAMPLE 1

The bleaching agents were evaluated as follows:

(1) Synthetic hydroxyapatite discs were polished and placed in sterile saliva at 37° C. overnight to form a pellicle.

(2) Discs were stained with tea solution for seven days at 37° C.

(3) Stained discs were immersed in bleaching solutions for desired time.

(4) The change in colour of the discs was measured using a Minolta chromameter CR-300 in L*a*b* mode. Using L* (initial), L* (soiled), and L* (cleaned), the percentage of stain removed was calculated. A negative value indicates a darkening and a positive value indicates a bleaching (whitening) effect.

All formulations used were made up in 0.5 M NaHCO3. A negative value indicates a darkening and Table 1 below shows the use of picolinic acid alone and together with either 0.1% H2O2 or PAP.

|  | % Stain Removed 10 mins |
| --- | --- |
| 0.1% H2O2 | 2 |
| 0.5 0.1% H2O2/5% picolinic acid | 13 |
| 1% PAP | 27 |
| 1% PAP/5% picolinic acid | 46 |
| 5% picolinic acid | 8 |

The results detailed in the table, show that the addition of a picolinic acid to the peracid provides a more effective bleaching composition over picolinic acid or the peracid alone.

EXAMPLE 2

The following oral composition comprises two formulations: a PAP-gel formulation and a pH-adjusting formulation.

PAP-gel Formulation

| Ingredient | Amount (% w/w) |
| --- | --- |
| PAP | 0.6 |
| Gantrez | 3.0 |
| Xanthan | 0.2 |
| Silica | 9.0 |
| Sodium hydroxide | 0.5 |
| Water | to 100 |

PAP is commercially available as Eureco HC-17 (ex. Ausimont).

This formulation has a pH of 4.

pH-adjusting Formulation

| Ingredient | Amount % (w/w) |
| --- | --- |
| Gantrez | 3.0 |
| Xanthan | 0.2 |
| Silica | 6.0 |
| picolinic acid | 5.0 |
| Saccharin | 0.25 |
| pH agent (TSP or NaOH) | to pH 11 |
| KNO3 | 5.0 |
| NaF/SMFP | to 1500 ppm |
| Colour | as appropriate |
| Water | to 100 |

When both the PAP-formulation and the pH-adjusting formulation are mixed together the pH of the resulting composition is between about 6.5 and 8.5.

What is claimed is:

1. An oral composition comprisining picolinic acid and a peroxyl species or equivalent source thereof, wherein the molar ratio of picolinic acid to peroxyl species or equivalent source thereof is from 1:30 to 100:1; and an oral active selected from the group consisting of an anti-inflammatory agent, an anti-caries agent, a vitamin, a desensitising agent which is potassium nitrate, a flavor, a sweetening agent and combinations thereof in functionally effective amounts.

2. An oral composition as in claim 1, wherein the peroxyl species or equivalent source thereof is a peracid or a compound that produces hydrogen peroxide on dissolution in water.

3. An oral composition according to claim 1 and comprising an additional transition metal chelator.

4. An oral composition according to claim 1, wherein the composition comprises a transition metal chetator having a binding coefficient for iron (III) of greater than $10^{15}$.

5. An oral composition according to claim 1, wherein the composition comprises diethylenetriaminepentaacetic acid as a transition metal chelator.

6. An oral composition according to claim 1, wherein the molar ratio of picolinic acid to peroxyl species or equivalent source thereof is from 1:10 to 20:1.

7. An oral composition according to claim 1, wherein the picolinic acid is present at a level from 0.01% to 10% by weight of the composition of which it is a part.

8. An oral composition according to claim 1, wherein the picolinic acid is present at a level from 0.15% to 2.5% by weight of the composition of which it is a part.

9. An oral composition according to claim 1, wherein the peroxyl species or equivalent source thereof is present at a level from 0.0001% to 1.5% by weight of the composition of which it is a part.

10. An oral composition according to claim 1, wherein the peroxyl species or equivalent source thereof is present at a level from 0.003% to 0.5% by weight of the composition of which it is a part.

11. An oral composition according to claim 1 and comprising a cosmetically acceptable carrier material.

12. A method applied to an oral cavity for a treatment selected from the group consisting of tooth whitening, anti-plaque, anti-malodour, anti-caries and anti-tartar by inclusion into an oral care regime of an oral composition according to claim 1 and applying the oral composition to the teeth.

\* \* \* \* \*